US011589757B2

(12) United States Patent
Kawabata et al.

(10) Patent No.: US 11,589,757 B2
(45) Date of Patent: Feb. 28, 2023

(54) BLOOD PRESSURE ESTIMATION DEVICE

(71) Applicants: OMRON Corporation, Kyoto (JP); OMRON HEALTHCARE Co., Ltd., Kyoto (JP)

(72) Inventors: Yasuhiro Kawabata, Kyoto (JP); Naomi Matsumura, Kyoto (JP); Naoki Matsumoto, Kyoto (JP)

(73) Assignees: OMRON CORPORATION, Kyoto (JP); OMRON HEALTHCARE CO., LTD., Kyoto (JP)

(*) Notice: Subject to any disclaimer, the term of this patent is extended or adjusted under 35 U.S.C. 154(b) by 408 days.

(21) Appl. No.: 16/813,904

(22) Filed: Mar. 10, 2020

(65) Prior Publication Data

US 2020/0205678 A1 Jul. 2, 2020

Related U.S. Application Data

(63) Continuation of application No. PCT/JP2018/030411, filed on Aug. 16, 2018.

(30) Foreign Application Priority Data

Sep. 12, 2017 (JP) .............................. JP2017-174919

(51) Int. Cl.
A61B 5/021 (2006.01)
A61B 5/00 (2006.01)
(Continued)

(52) U.S. Cl.
CPC ........ A61B 5/02116 (2013.01); A61B 5/0022 (2013.01); A61B 5/022 (2013.01);
(Continued)

(58) Field of Classification Search
None
See application file for complete search history.

(56) References Cited

U.S. PATENT DOCUMENTS 11,183,303 B2 * 11/2021 Matichuk ......... G06K 19/07762
2009/0216132 A1 8/2009 Orbach
(Continued)

FOREIGN PATENT DOCUMENTS

CN 101547634 9/2009
CN 106618537 5/2017
(Continued)

OTHER PUBLICATIONS

International Search Report of the International Searching Authority for PCT/JP2018/030411 dated Sep. 25, 2018.
(Continued)

Primary Examiner — Hongmin Fan
(74) Attorney, Agent, or Firm — Wenderoth, Lind & Ponack, L.L.P.

(57) ABSTRACT

A blood pressure estimation device includes a display unit (10), a belt portion (20), a first contact electrode (61) and a second contact electrode (62) for detecting an electrocardiographic waveform, and a pulse wave sensor. The display unit (10) displays a blood pressure estimation result. The belt portion (20) is connected to the display unit (10) and surrounds a target measurement site. The pulse wave sensor includes a pulse wave detection unit (40E) that detects a pulse wave of an artery (91) passing through the target measurement site. The first contact electrode (61) and the pulse wave detection unit (40E) are provided on an inner circumferential portion (20a) of the belt portion (20). The second contact electrode (62) is provided on an outer circumferential portion (20b) of the belt portion (20). The first contact electrode (61) and the pulse wave detection unit (40E) are provided in a position where the first contact electrode (61) and the pulse wave detection unit (40E) are to be pressed against the target measurement site when the
(Continued)

second contact electrode (62) is pressed from an outer circumferential side of the belt portion (20).

8 Claims, 10 Drawing Sheets

(51) Int. Cl.
    *A61B 5/022*     (2006.01)
    *A61B 5/0295*     (2006.01)
    *A61B 5/339*     (2021.01)

(52) U.S. Cl.
    CPC ............ *A61B 5/0295* (2013.01); *A61B 5/339* (2021.01); *A61B 5/6831* (2013.01); *A61B 5/742* (2013.01); *A61B 2562/0247* (2013.01)

(56) References Cited

U.S. PATENT DOCUMENTS

| | | |
|---|---|---|
| 2010/0049059 A1 | 2/2010 | Ha et al. |
| 2010/0076328 A1 | 3/2010 | Matsumura et al. |
| 2010/0130876 A1 | 5/2010 | Cho |
| 2013/0190576 A1 | 7/2013 | Matsumura et al. |
| 2014/0257049 A1 | 9/2014 | Soundarapandian et al. |
| 2015/0119654 A1 | 4/2015 | Martin et al. |
| 2015/0157220 A1 | 6/2015 | Fish et al. |
| 2015/0160048 A1 | 6/2015 | Schuessler |
| 2015/0366469 A1 | 12/2015 | Harris et al. |
| 2016/0089081 A1* | 3/2016 | Morris ................. A61B 5/0082 600/382 |
| 2016/0270668 A1 | 9/2016 | Gil |
| 2016/0287172 A1 | 10/2016 | Morris et al. |
| 2016/0353998 A1 | 12/2016 | Lee et al. |
| 2017/0095171 A1* | 4/2017 | Park .................... A61B 5/02125 |
| 2017/0215749 A1* | 8/2017 | Zhuo ................. A61B 5/02055 |
| 2017/0224226 A1 | 8/2017 | Kitagawa et al. |
| 2017/0251935 A1 | 9/2017 | Yuen |
| 2018/0353089 A1 | 12/2018 | Choi et al. |

FOREIGN PATENT DOCUMENTS

| | | |
|---|---|---|
| CN | 106714674 | 5/2017 |
| CN | 107072562 | 8/2017 |
| JP | H10243929 A | 9/1998 |
| JP | 2008536545 A | 9/2008 |
| JP | 2009072242 A | 4/2009 |
| JP | 2010-046494 | 3/2010 |
| JP | 2013150691 A | 8/2013 |
| JP | 2015-112488 | 6/2015 |
| JP | 2016-536040 | 11/2016 |
| JP | 2017500069 A | 1/2017 |
| KR | 10-2011-0012784 | 2/2011 |
| KR | 10-2017-0067131 | 6/2017 |

OTHER PUBLICATIONS

Translation of the International Search Report of the International Searching Authority for PCT/JP2018/030411 dated Sep. 25, 2018.
Notice of Grounds of Rejection dated Feb. 16, 2021 in counterpart Japanese Application No. 2017-174919 with English translation.
Office Action dated Mar. 14, 2022 in corresponding Chinese Patent Application No. 201880058349.7, with English language translation.

* cited by examiner

BLOOD PRESSURE ESTIMATION DEVICE

CROSS-REFERENCE TO RELATED APPLICATIONS

This is a continuation of International Application JP 2017-174919 filed on Sep. 12, 2017 and PCT/JP2018/030411, with an international filing date of Aug. 16, 2018, filed by applicant, the disclosure of which is hereby incorporated by reference in its entirety.

TECHNICAL FIELD

The present invention relates to a blood pressure estimation device, and particularly relates to a blood pressure estimation device that estimates blood pressure based on a transit time of a pulse wave.

BACKGROUND ART

JP 2017-500069 T (Patent Document 1) is a document in the related art that discloses a mobile device capable of estimating blood pressure by using a photoplethysmography (PPG) measurement value by PPG, an electrocardiography (ECG) measurement value by ECG, and a pulse transit time (PTT).

The mobile device described in Patent Document 1 includes an outer cover, a processor, and a plurality of sensors physically coupled to the outer cover. At least one of the plurality of sensors is configured to obtain a PPG measurement value, and is accommodated in a contact button coupled to the outer cover. At least one of the plurality of sensors is configured to obtain an ECG measurement value, and includes a first electrode and a second electrode. The first electrode and the second electrode are contact electrodes that contact a body of a subject in order to obtain the ECG measurement value.

CITATION LIST

Patent Literature

Patent Document 1: JP 2017-500069 T

SUMMARY OF INVENTION

Technical Problem

In the mobile device described in Patent Document 1, each of the contact button, the first electrode, and the second electrode is provided on a display unit having a display function. In general, an outer portion of the display unit is constituted of a rigid member and has a constant shape, and thus it is difficult to bring the contact electrode for obtaining an ECG measurement value into close contact with a target measurement site. When the contact electrode for obtaining an ECG measurement value is not in close contact with a target measurement site, accuracy of a blood pressure estimation result decreases.

The present invention has been made in view of the above-mentioned problems, and an object thereof is to provide a blood pressure estimation device with high accuracy capable of bringing a contact electrode for obtaining an ECG measurement value into close contact with a target measurement site.

Solution to Problem

A blood pressure estimation device based on the present invention includes a display unit, a belt portion, a first contact electrode and a second contact electrode for detecting an electrocardiographic waveform, and a pulse wave sensor. The display unit is configured display blood pressure estimation result. The belt portion is connected to the display unit and surrounds a target measurement site. The pulse wave sensor includes a pulse wave detection unit configured to detect a pulse wave of an artery passing through the target measurement site. The first contact electrode and the pulse wave detection unit are provided on an inner circumferential portion of the belt portion. The second contact electrode is provided on an outer circumferential portion of the belt portion. The first contact electrode and the pulse wave detection unit are provided in a position where the first contact electrode and the pulse wave detection unit are to be pressed against the target measurement site when the second contact electrode is pressed from an outer circumferential side of the belt portion.

In one aspect of the present invention, at least a part of the pulse wave detection unit and at least a part of the second contact electrode face each other with the belt portion interposed therebetween.

In one aspect of the present invention, the belt portion includes a belt body, and a fluid bag that is provided on an inner circumferential side of the belt body and are inflatable and deflatable. A pressure detection unit configured to detect pressure in the fluid bag for a blood pressure measurement by an oscillometric method is provided in the fluid bag. The first contact electrode and the pulse wave detection unit are provided on an external surface portion of the fluid bag that constitutes the inner circumferential portion of the belt portion. The second contact electrode is provided on an external surface portion of the belt body that constitutes the outer circumferential portion of the belt portion.

In one aspect of the present invention, the belt portion further includes a solid member disposed between the belt body and the fluid bag. The solid member faces at least a part of the second contact electrode with the belt body interposed therebetween, and faces at least a part of the pulse wave detection unit with the fluid bag interposed therebetween.

In one aspect of the present invention, the solid member is curved so as to conform to a shape of the target measurement site.

In one aspect of the present invention, the pulse wave detection unit detect a pulse wave based on a change in impedance of the artery passing through the target measurement site.

In one aspect of the present invention, a notification unit configured to notify a determination result of whether or not detection accuracy of a pulse wave by the pulse wave detection unit satisfies a reference value is further provided.

In one aspect of the present invention, the second contact electrode is located, on the outer circumferential portion of the belt portion in a state of surrounding the target measurement site, on a side opposite to the display unit in a circumferential direction of the belt portion.

Advantageous Effects of Invention

According to the present invention, a contact electrode for obtaining an ECG measurement value can be brought into close contact with a target measurement site, and accuracy of a blood pressure estimation device can be increased.

DESCRIPTION OF EMBODIMENTS

Figure 1:
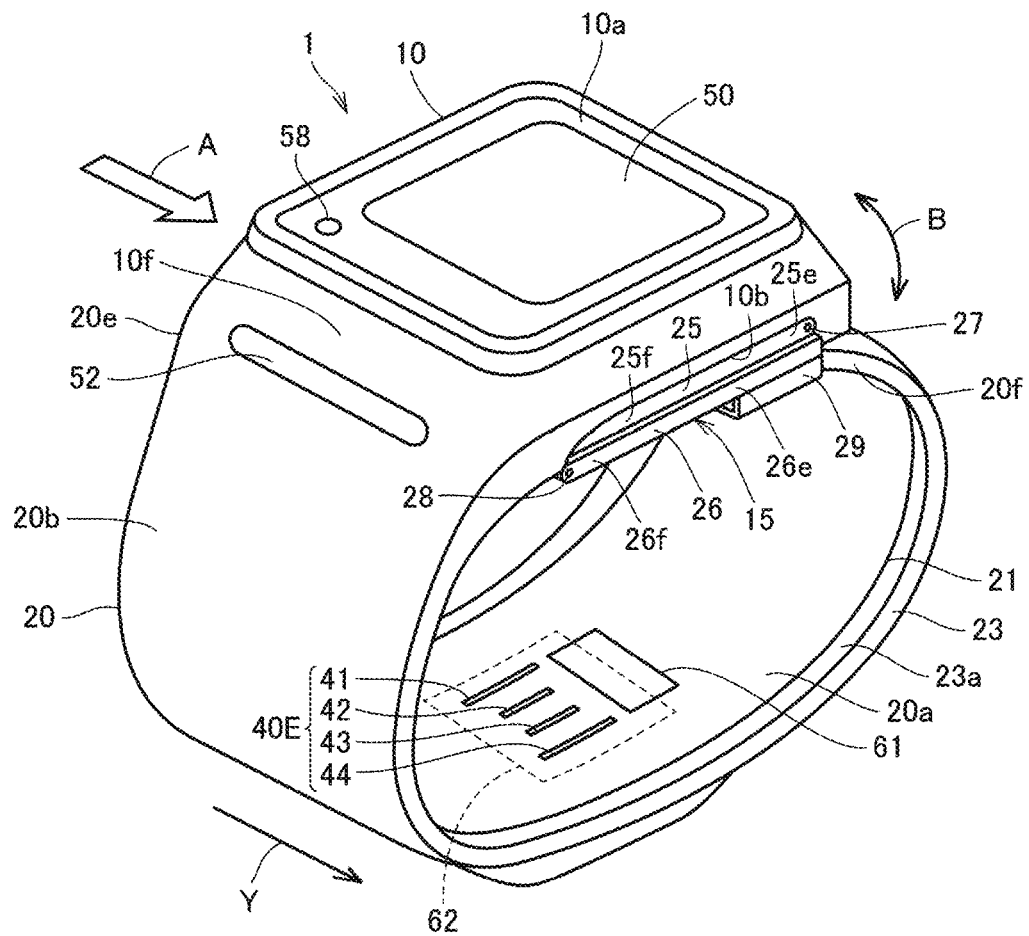
FIG. 1 is a perspective view illustrating an appearance of a blood pressure estimation device according to a first embodiment of the present invention.

A blood pressure estimation device according to each embodiment of the present invention will be described below with reference to the drawings. In the following description of the embodiments, the same or corresponding portions in the drawings are denoted by the same reference signs, and the description thereof is not repeated.

First Embodiment

Figure 2:
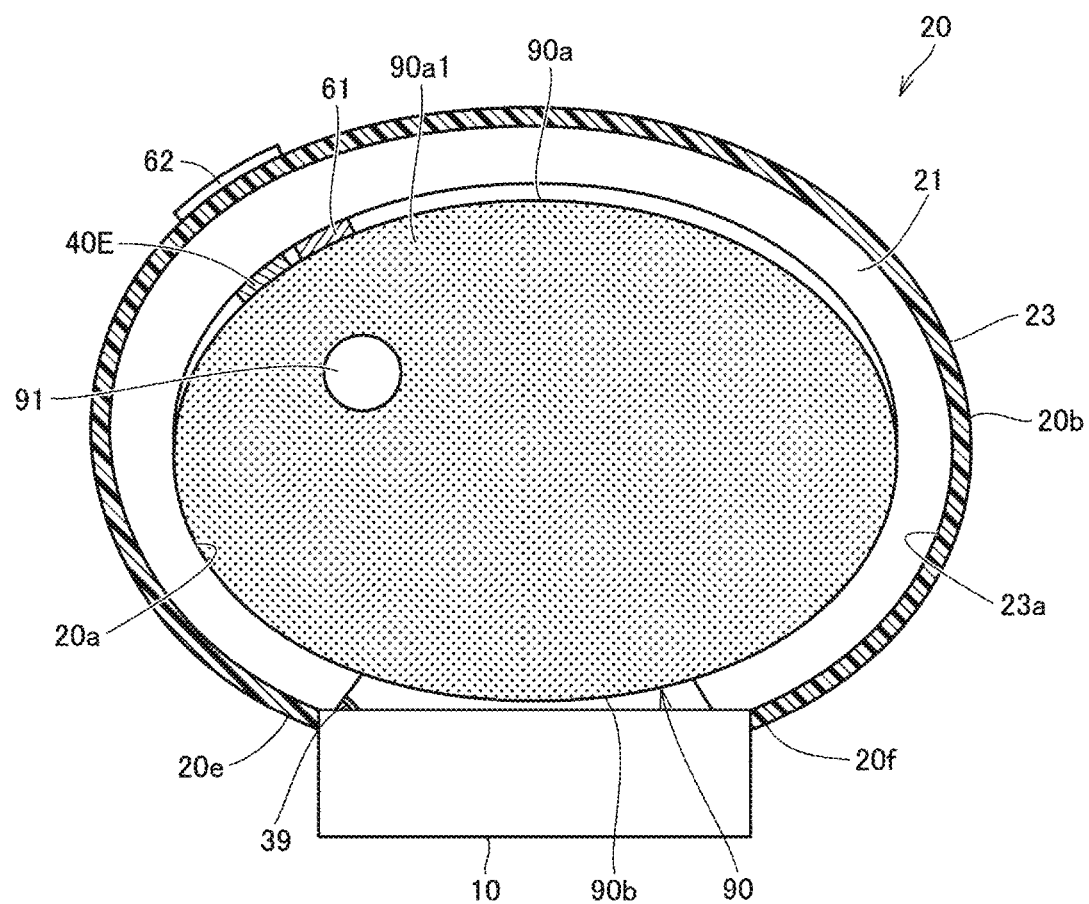
FIG. 2 is a cross-sectional view illustrating a state in which the blood pressure estimation device according to the first embodiment of the present invention is attached to a target measurement site.

FIG. 1 is a perspective view illustrating an appearance of a blood pressure estimation device according to a first embodiment of the present invention. FIG. 2 is a cross-sectional view illustrating a state in which the blood pressure estimation device according to the first embodiment of the present invention is attached to a target measurement site. In FIG. 2, the cross section perpendicular to a longitudinal direction of a left wrist is illustrated. In the present embodiment, the target measurement site is the left wrist. Note that the target measurement site may be a right wrist.

As illustrated in FIGS. 1 and 2, a blood pressure estimation device 1 according to the first embodiment of the present invention includes a display unit 10, a belt portion 20, a first contact electrode 61 and a second contact electrode 62 for detecting an electrocardiographic waveform, and a pulse wave sensor.

The display unit 10 displays a blood pressure estimation result of the blood pressure estimation device 1. The belt portion 20 is connected to the display unit 10, and surrounds a left wrist 90 that is a target measurement site. The pulse wave sensor includes a pulse wave detection unit 40E that detects a pulse wave of an artery passing through the target measurement site.

The blood pressure estimation device 1 is broadly constituted of the belt portion 20 that surrounds the left wrist 90 being the target measurement site, and the display unit 10 connected to the belt portion 20.

As illustrated in FIG. 1, the display unit 10 has a truncated quadrangular pyramid that protrudes outward from the belt portion 20. The display unit 10 is preferably small and thin so as not to interfere with activity of a subject.

A display 50, a notification unit 58, and an operating section 52 are provided on the display unit 10. The display 50 and the notification unit 58 are disposed on a top surface portion 10a of the display unit 10. The operating section 52 is disposed on a side surface portion 10f of the display unit 10.

The display unit 10 is integrally formed with one end portion 20e of the belt portion 20 by integral molding. Note that the belt portion 20 and the display unit 10 may be formed separately, and the display unit 10 and the belt portion 20 may be configured to be connected to each other by an engagement member such as a hinge, for example. As illustrated in FIG. 1, a bottom surface 10b of the display unit 10 and an end portion 20f of the belt portion 20 are connected to each other by a buckle 15.

The buckle 15 includes a plate-like member 25 disposed on an outer circumferential side and a plate-like member 26 disposed on an inner circumferential side. One end portion 25e of the plate-like member 25 is freely rotatably attached to the display unit 10 via a connecting rod 27 that extends along a width direction Y. The other end portion 25f of the plate-like member 25 is freely rotatably attached to the other end portion 26f of the plate-like member 26 via a connecting rod 28 that extends along the width direction Y. One end portion 26e of the plate-like member 26 is fixed to the vicinity of the end portion 20f of the belt portion 20 by a fixing portion 29.

An attachment position of the fixing portion 29 in regard to a circumferential direction of the belt portion 20 is previously adjusted in accordance with a circumferential length of the left wrist 90 of the subject. The blood pressure estimation device 1 has a substantially annular shape as a whole. The buckle 15 is configured to be able to open and close between the bottom surface 10b of the display unit 10 and the end portion 20f of the belt portion 20 in a direction of an arrow B in FIG. 1.

The belt portion 20 includes a belt body 23, and a fluid bag 21 that is provided on the inner circumferential side of the belt body 23 and is inflatable and deflatable. A dimension in the width direction Y of the belt portion 20 is, for example, approximately 30 mm. The belt body 23 is an elongate band-like member that surrounds the left wrist 90 along the circumferential direction. The belt body 23 includes an outer circumferential portion 20b. The belt body 23 is formed of a plastic material having flexibility with respect to a thickness direction and having non-elasticity with respect to the circumferential direction.

The fluid bag 21 is attached along an inner circumferential portion 23a of the belt body 23 and has an external surface portion constituting an inner circumferential portion 20a of the belt portion 20 that contacts the left wrist 90. The fluid bag 21 is formed in a bag shape that can accommodate a fluid by welding edge portions of two stretchable polyurethane sheets overlapping each other. The fluid includes both a liquid and a gas, and, for example, water, air, and the like can be used as the fluid. The blood pressure estimation device 1 is provided with a pressure sensor that detects pressure in the fluid bag 21.

The first contact electrode 61 and the pulse wave detection unit 40E of the pulse wave sensor are provided on the inner circumferential portion 20a of the belt portion 20 between one end portion 20e and the other end portion 20f of the belt portion 20. In the present embodiment, the first contact electrode 61 and the pulse wave detection unit 40E of the pulse wave sensor are provided on the external surface portion of the fluid bag 21 constituting the inner circumferential portion 20a of the belt portion 20.

The pulse wave detection unit 40E of the pulse wave sensor is constituted of four electrodes that are spaced apart from each other in the width direction Y of the belt portion 20. Specifically, in order from one side in the width direction Y, a current electrode 41, a detection electrode 42, a detection electrode 43, and a current electrode 44 are arranged in one row. An interval between the detection electrode 42 and the detection electrode 43 in the width direction Y of the belt portion 20 is 2 mm, for example. Each of the current electrode 41, the detection electrode 42, the detection electrode 43, and the current electrode 44 has a rectangular outer shape and is formed to be thin and flexible.

With the blood pressure estimation device 1 attached to the left wrist 90, the pulse wave detection unit 40E is disposed corresponding to a radial artery 91 of the left wrist 90. Note that the radial artery 91 passes, in the left wrist 90, through the vicinity of a palm side surface 90a of the left wrist 90 that is a surface on a palm side of a hand. In the present embodiment, the pulse wave detection unit 40E detects a pulse wave based on a change in impedance of the radial artery 91 passing through the left wrist 90.

Note that a method for detecting a pulse wave by the pulse wave detection unit is not limited to a method for detecting a pulse wave from a change in impedance of an artery. For example, the pulse wave sensor may include a light emitting element that illuminates light toward an artery passing through a corresponding portion of a target measurement site, and a light receiving element that receives reflected light or transmitted light of the light, and may detect a change in arterial volume of as a pulse wave.

Alternatively, the pulse wave sensor may include a piezoelectric sensor abutting a target measurement site, and detect a strain due to pressure of an artery passing through a corresponding portion of the target measurement site as a change in electrical resistance. Furthermore, the pulse wave sensor may include a transmission element that transmits an electromagnetic wave toward an artery passing through a corresponding portion of a target measurement site, and a reception element that receives a reflected wave of the electromagnetic wave, and may detect a change in distance between the artery and the sensor by a pulse wave of the artery as a phase shift between the transmission wave and the reflected wave.

The first contact electrode 61 is disposed adjacent to the pulse wave detection unit 40E of the pulse wave sensor in the circumferential direction of the belt portion 20. The first contact electrode 61 has a rectangular shape and is formed to be thin and flexible.

The second contact electrode 62 is provided on the outer circumferential portion 20b of the belt portion 20 between one end portion 20e and the other end portion 20f of the belt portion 20. In the present embodiment, the second contact electrode 62 is provided on an external surface portion of the belt body 23 that constitutes the outer circumferential portion 20b of the belt portion 20. The second contact electrode 62 is located, on the outer circumferential portion 20b of the belt portion 20 in a state of surrounding the target measurement site, on a side opposite to the display unit 10 in the circumferential direction of the belt portion 20. The second contact electrode 62 has a rectangular outer shape and is formed to be thin and flexible.

At least a part of the pulse wave detection unit 40E and at least a part of the second contact electrode 62 face each other with the belt portion 20 interposed therebetween. In the present embodiment, the entirety of the pulse wave detection unit 40E faces the second contact electrode 62 with the belt portion 20 interposed therebetween. A part of the first contact electrode 61 faces the second contact electrode 62 with the belt portion 20 interposed therebetween. Note that the entirety of the first contact electrode 61 may face the second contact electrode 62 with the belt portion 20 interposed therebetween.

When the subject attaches the blood pressure estimation device 1 to the left wrist 90, the subject passes a left hand through the belt portion 20 from a direction indicated by an arrow A in FIG. 1 with the buckle 15 open to increase an annular diameter of the belt portion 20. Next, as illustrated in FIG. 2, the subject adjusts an angular position of the belt portion 20 around the left wrist 90, and positions the pulse wave detection unit 40E of the pulse wave sensor so as to face the radial artery 91 passing through the left wrist 90.

This brings the pulse wave detection unit 40E of the pulse wave sensor into a state of abutting a portion 90a1 of the palm side surface 90a of the left wrist 90 that corresponds to the radial artery 91. In this state, the subject closes and fixes the buckle 15. In this way, the subject attaches the blood pressure estimation device 1 to the left wrist 90. With the blood pressure estimation device 1 attached to the left wrist 90, the display unit 10 is disposed corresponding to a back side surface 90b of the left wrist 90 that is a surface on a back side of the hand.

Figure 3:
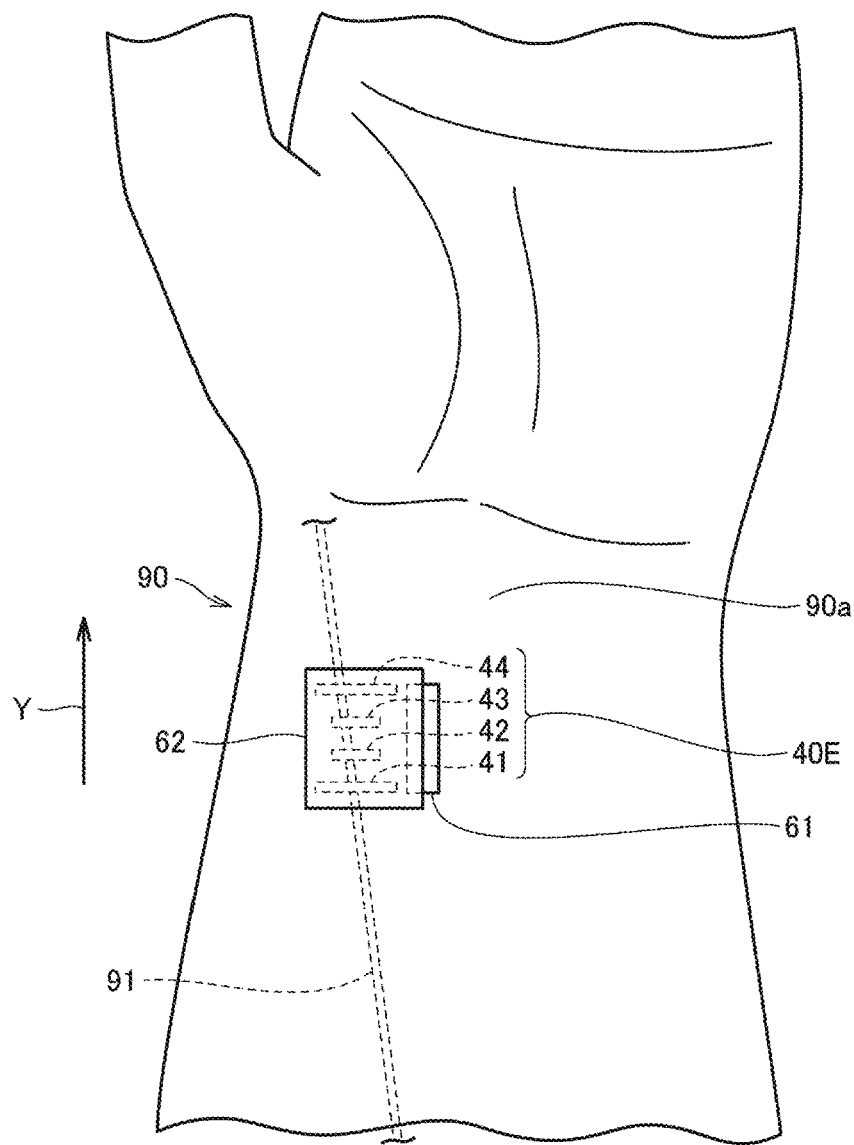
FIG. 3 is a diagram illustrating an arrangement of a pulse wave detection unit of a pulse wave sensor, a first contact electrode, and a second contact electrode with the blood pressure estimation device according to the first embodiment of the present invention attached to the target measurement site.

FIG. 3 is a diagram illustrating an arrangement of the pulse wave detection unit of the pulse wave sensor, the first contact electrode, and the second contact electrode with the blood pressure estimation device according to the first embodiment of the present invention attached to the target measurement site. As illustrated in FIG. 3, with the blood pressure estimation device 1 attached to the left wrist 90, the pulse wave detection unit 40E of the pulse wave sensor is located along the radial artery 91.

Figure 4:
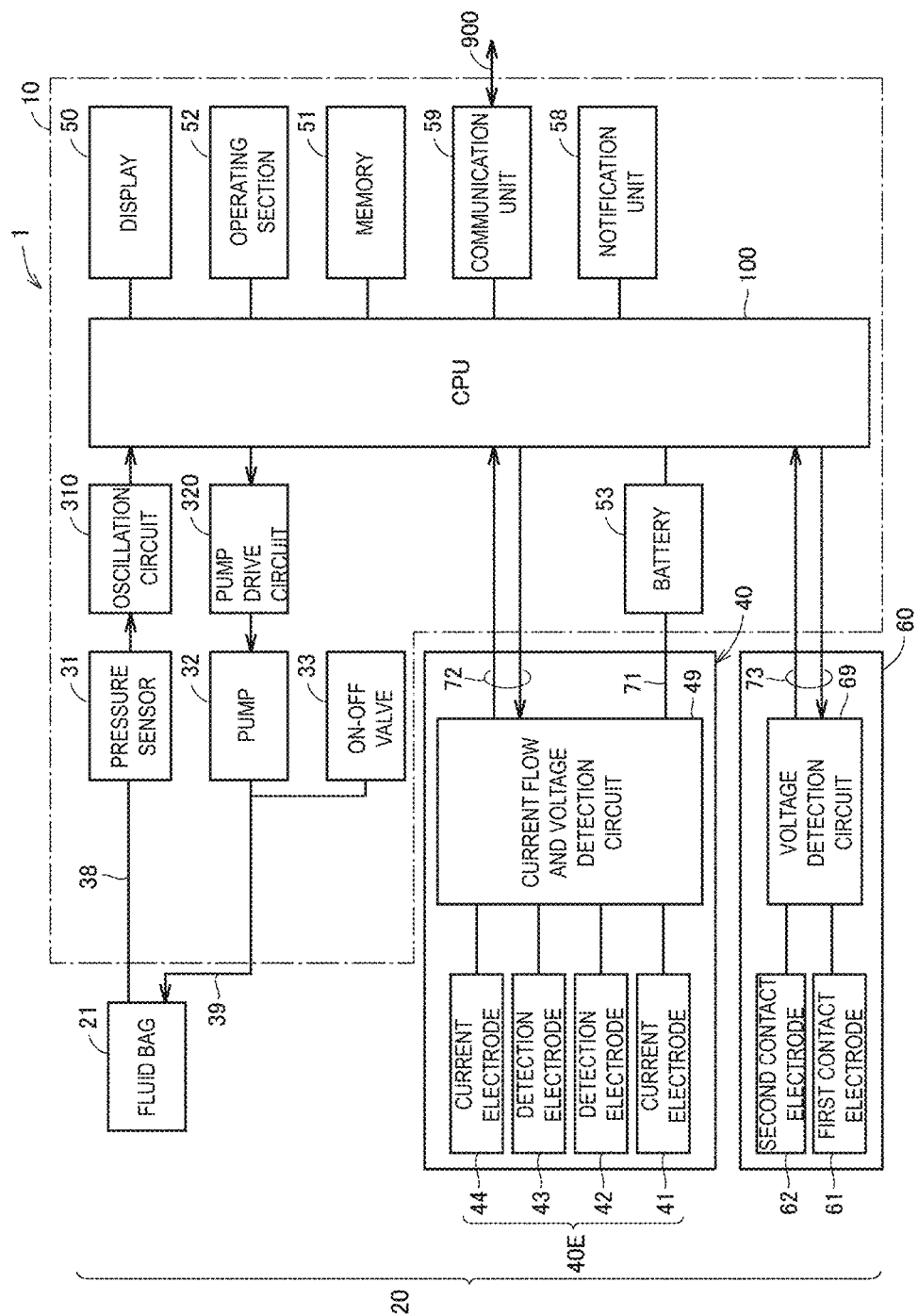
FIG. 4 is a block diagram illustrating a configuration of the blood pressure estimation device according to the first embodiment of the present invention.

Herein, each configuration of the blood pressure estimation device 1 will be described in detail. FIG. 4 is a block diagram illustrating the configuration of the blood pressure estimation device according to the first embodiment of the present invention.

As illustrated in FIG. 4, the display unit 10 is provided with a central processing unit (CPU) 100, the display 50, a memory 51, the operating section 52, a battery 53, and a communication unit 59. Further, the display unit 10 is provided with a pressure sensor 31, a pump 32, and an on-off valve 33. Furthermore, the display unit 10 is provided with an oscillation circuit 310 that converts an output of the pressure sensor 31 to a frequency, and a pump drive circuit 320 that drives the pump 32.

The pulse wave sensor 40 includes the pulse wave detection unit 40E and a current flow and voltage detection circuit 49. Each of the current electrode 41, the detection electrode 42, the detection electrode 43, and the current electrode 44 is connected to the current flow and voltage detection circuit 49. The current flow and voltage detection circuit 49 is connected to the CPU 100 through a signal wire 72.

An ECG measurement unit 60 for detecting an electrocardiographic waveform includes the first contact electrode 61, the second contact electrode 62, and a voltage detection circuit 69. Each of the first contact electrode 61 and the second contact electrode 62 is connected to the voltage detection circuit 69. The voltage detection circuit 69 is connected to the CPU 100 through a signal wire 73.

The display 50 is constituted of, for example, an organic electro luminescence (EL) display, and displays information about blood pressure estimates, such as a blood pressure estimation result, and other information according to a control signal from the CPU 100. Note that the display 50 is not limited to an organic EL display, and may be constituted of other types of displays such as a liquid crystal display (LCD), for example.

The operating section 52 is constituted of, for example, a push switch, and inputs, to the CPU 100, an operation signal according to an instruction to start or stop the blood pressure estimation by the subject. Note that the operating section 52 is not limited to a push switch, and may be, for example, a pressure sensitive touch panel switch, a capacitive touch panel switch, and the like. Further, a microphone may be provided in the display unit 10, and an instruction to start or stop the blood pressure estimation by sound of the subject may be input to the CPU 100 via the microphone.

The memory 51 non-temporarily stores a program for controlling the blood pressure estimation device 1, data used for controlling the blood pressure estimation device 1, settings data for setting various functions of the blood pressure estimation device 1, data about an estimated result of a blood pressure value, and the like. Further, the memory 51 is used as a working memory and the like when the program is executed.

The CPU 100 controls various functions of the blood pressure estimation device 1 according to the program for controlling the blood pressure estimation device 1 stored in the memory 51. For example, when performing a blood pressure measurement by the oscillometric method, the CPU 100 causes the pump 32 to be driven and the on-off valve 33 to be brought into a closed state based on a signal from the pressure sensor 31 in response to an instruction to start the blood pressure measurement from the operating section 52. The CPU 100 calculates a blood pressure value based on the signal from the pressure sensor 31.

When performing blood pressure estimation based on a pulse transit time, the CPU 100 brings the on-off valve 33 into an open state in order to cause air in the fluid bag 21 to be discharged in response to an instruction to start the blood pressure estimation from the operating section 52.

The communication unit 59 is controlled by the CPU 100 and transmits predetermined information to an external device through a network 900, or transmits information received from an external device through the network 900 to the CPU 100. The communication performed through the network 900 may be wireless or wired. For example, the network 900 is the Internet, but is not limited thereto, and may be other types of networks, such as a local area network (LAN), or may be one-to-one communication using a USB cable and the like. The communication unit 59 may include a micro USB connector.

The notification unit 58 notifies a determination result of whether or not detection accuracy of a pulse wave by the pulse wave detection unit 40E satisfies a reference value as described later. The notification unit 58 is constituted of a light emitting diode (LED) light, a speaker, or the like.

The pump 32 and the on-off valve 33 are connected to the fluid bag 21 through an air pipe 39. The pump 32 is, for example, a piezoelectric pump. The pump 32 supplies air into the fluid bag 21 through the air pipe 39 in order to pressurize the inside of the fluid bag 21.

The pressure sensor 31 is connected to the fluid bag 21 through an air pipe 38. The pressure sensor 31 detects pressure in the fluid bag 21 through the air pipe 38. The pressure sensor 31 is, for example, a piezoresistive pressure sensor. The pressure sensor 31 outputs, as a time series signal, pressure detected with atmospheric pressure as a zero point, for example.

The on-off valve 33 is mounted on the pump 32 and is configured to open and close in conjunction with driving of the pump 32. Specifically, the on-off valve 33 is closed while the pump 32 is driven. During this time, air is encapsulated in the fluid bag 21. The on-off valve 33 is open while the pump 32 is stopped. During this time, air in the fluid bag 21 is discharged into the atmosphere through the air pipe 39. The on-off valve 33 functions as a check valve, and the discharged air does not flow back.

The pump drive circuit 320 drives the pump 32 based on a control signal provided from the CPU 100.

The oscillation circuit 310 outputs, to the CPU 100, a frequency signal having a frequency in accordance with an electrical signal value based on a change in electrical resistance due to a piezoresistive effect from the pressure sensor 31. The output of the pressure sensor 31 is used for controlling the pressure in the fluid bag 21 and calculating a blood pressure value by the oscillometric method. Blood pressure values by the oscillometric method include systolic blood pressure (SBP) and diastolic blood pressure (DBP).

The battery 53 supplies power to various elements mounted on the display unit 10. The battery 53 also supplies power to the current flow and voltage detection circuit 49 of the pulse wave sensor 40 through a wire 71. The wire 71 is provided extending between the display unit 10 and the pulse wave sensor 40 along the circumferential direction of the belt portion 20 while being interposed together with the signal wire 72 between the belt body 23 of the belt portion 20 and the fluid bag 21. The battery 53 is also connected to the CPU 100.

Hereinafter, an operation of the blood pressure estimation device 1 according to the first embodiment of the present invention when blood pressure is estimated by using the blood pressure estimation device 1 will be described.

Figure 5:
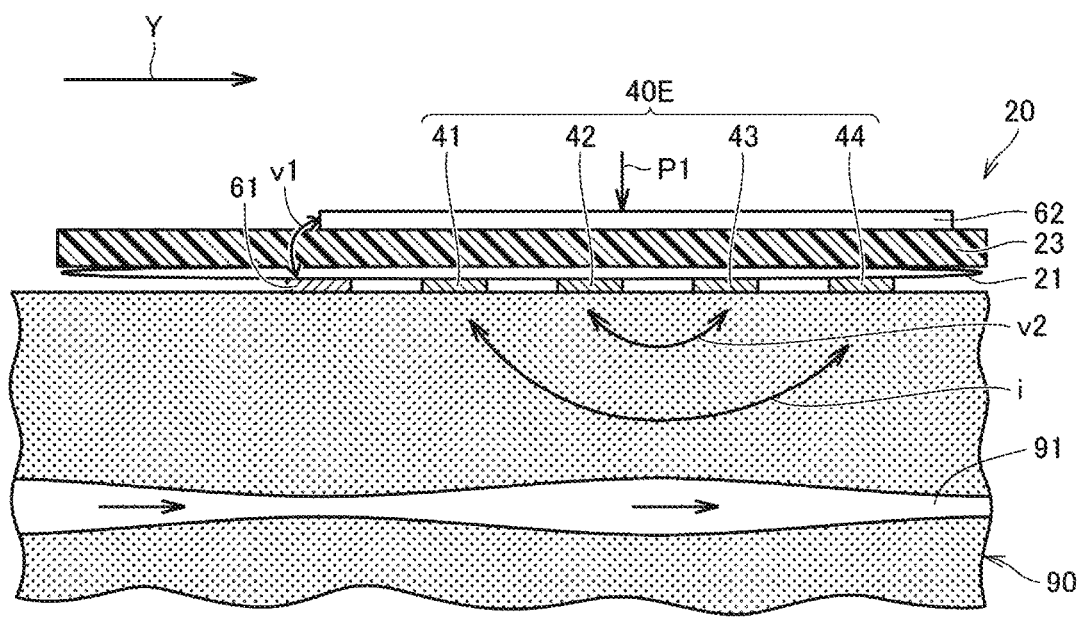
FIG. 5 is a cross-sectional view illustrating a state in which the blood pressure estimation device according to the first embodiment of the present invention is attached to the target measurement site and measures a pulse transit time.
Figure 6:
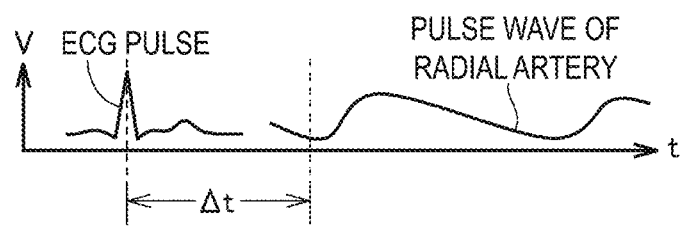
FIG. 6 is a diagram illustrating a pulse transit time between an ECG pulse and a pulse wave of a radial artery that are detected by the blood pressure estimation device according to the first embodiment of the present invention.

FIG. 5 is a cross-sectional view illustrating a state in which the blood pressure estimation device according to the first embodiment of the present invention is attached to the target measurement site and measures a pulse transit time. FIG. 6 is a diagram illustrating a pulse transit time between an ECG pulse and a pulse wave of a radial artery that are detected by the blood pressure estimation device according to the first embodiment of the present invention. In FIG. 5, the cross section along the longitudinal direction of the left wrist is illustrated. Note that a position of the first contact electrode 61 is changed and illustrated for convenience of description. In FIG. 6, a vertical axis indicates voltage (V), and a horizontal axis indicates time.

First, when the ECG pulse and the pulse wave of the radial artery 91 are detected, the fluid bag 21 is in an unpressurized state by discharging air in the fluid bag 21 as illustrated in FIG. 5.

The subject presses the second contact electrode 62 with a finger of a right hand in order to detect the ECG pulse. As a result, as illustrated in FIG. 5, a pressing force P1 is applied to the second contact electrode 62, and the pulse wave detection unit 40E is pressed against the target measurement site. In other words, the pulse wave detection unit 40E is provided in a position where the pulse wave detection unit 40E is pressed against the target measurement site when the second contact electrode 62 is pressed from the outer circumferential side of the belt portion 20. Note that the first contact electrode 61 is also pressed against the target measurement site by the pressing force P1 being applied to the second contact electrode 62. In other words, the first contact electrode 61 is provided in a position where the first contact electrode 61 is pressed against the target measurement site when the second contact electrode 62 is pressed from the outer circumferential side of the belt portion 20.

The voltage detection circuit 69 detects a voltage signal v1 between the first contact electrode 61 and the second contact electrode 62. The voltage signal v1 is output to the CPU 100 through the wire 73. The CPU 100 performs signal processing on the input voltage signal v1, and generates the ECG pulse illustrated in FIG. 6.

The current flow and voltage detection circuit 49 applies a voltage between the current electrode 41 and the current electrode 44, and flows a current i having a frequency of 50 kHz and a current value of 1 mA, for example, in order to detect the pulse wave of the radial artery substantially simultaneously with the detection of the ECG pulse. In this state, the current flow and voltage detection circuit 49 detects a voltage signal v2 between the detection electrode 42 and the detection electrode 43. The voltage signal v2 represents a change in electrical impedance due to a pulse wave of a blood flow of the radial artery 91 in a portion of the palm side surface 90a of the left wrist 90 facing the pulse wave detection unit 40E.

The voltage signal v2 is output to the CPU 100 through the wire 72. The CPU 100 performs signal processing on the input voltage signal v2, and generates the pulse wave of the radial artery illustrated in FIG. 6. Furthermore, the CPU 100 calculates a time difference $\Delta t$ between a peak of the ECG pulse and a rising time point of the pulse wave of the radial artery. This time difference $\Delta t$ is the pulse transit time. Note that the time difference $\Delta t$ between a peak of the ECG pulse and a peak of the pulse wave of the radial artery may be calculated as the pulse transit time.

Figure 7:
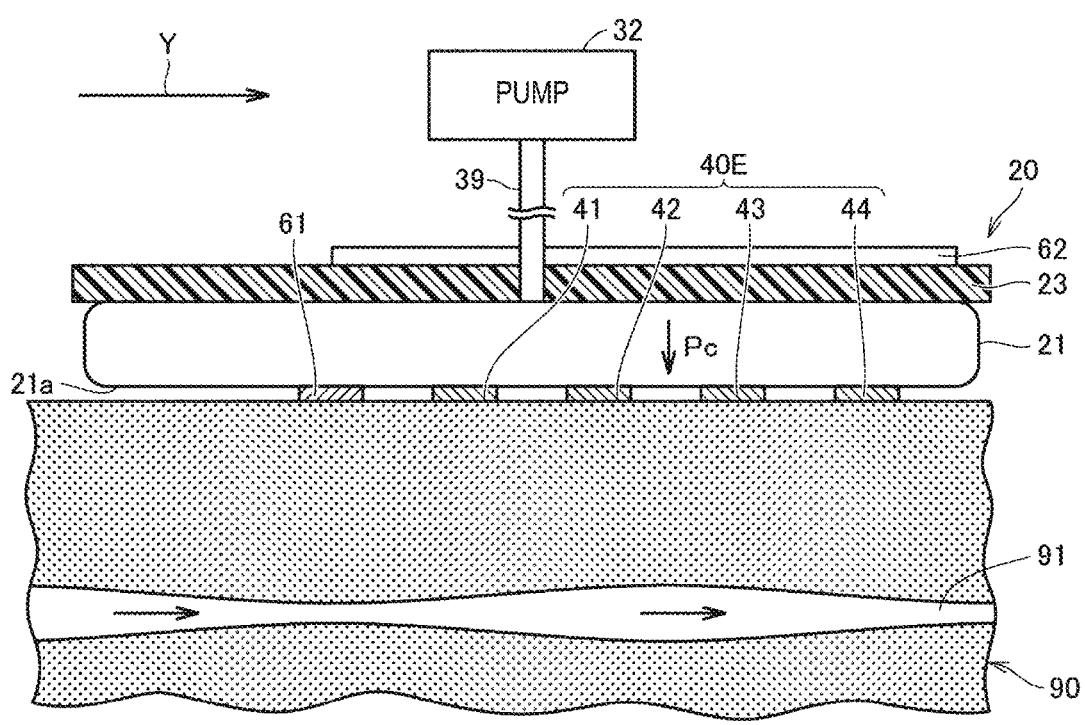
FIG. 7 is a cross-sectional view illustrating a state in which the blood pressure estimation device according to the first embodiment of the present invention is attached to the target measurement site and measures blood pressure by an oscillometric method.

FIG. 7 is a cross-sectional view illustrating a state in which the blood pressure estimation device according to the first embodiment of the present invention is attached to the target measurement site and measures blood pressure by the oscillometric method. In FIG. 7, the cross section along the longitudinal direction of the left wrist is illustrated.

When an instruction to start a blood pressure measurement is input from the operating section 52, the CPU 100 of the blood pressure estimation device 1 causes the pump 32 to be stopped through the pump drive circuit 320, opens the on-off valve 33 to cause air to be discharged in the fluid bag 21. Note that an output value of the pressure sensor 31 at present is set as a value corresponding to atmospheric pressure.

Then, the CPU 100 causes the on-off valve 33 to be closed, and the pump 32 to be driven through the pump drive circuit 320 to supply air into the fluid bag 21. This causes the fluid bag 21 to be expanded, and also gradually pressurizes the inside of the fluid bag 21. As illustrated in FIG. 7, the fluid bag 21 extends in the circumferential direction of the left wrist 90, and compresses the left wrist 90 in the circumferential direction with pressure Pc by being pressurized by the pump 32.

In the pressurization process, the CPU 100 monitors the pressure Pc in the fluid bag 21 by the pressure sensor 31 in order to calculate a blood pressure value, and acquires, as a pulse wave signal, a variable component of an arterial volume generated in the radial artery 91 of the left wrist 90.

The CPU 100 attempts to calculate a blood pressure value of each of systolic blood pressure and diastolic blood pressure based on the acquired pulse wave signal by applying a known algorithm by the oscillometric method. When the CPU 100 cannot yet calculate a blood pressure value due to a lack of data, the CPU 100 again attempts to calculate a blood pressure value by further causing the pressure Pc to be increased in the fluid bag 21 as long as the pressure Pc in the fluid bag 21 does not reach an upper pressure limit of, for example, approximately 300 mmHg.

When the blood pressure value can be calculated, the CPU 100 causes the pump 32 to be stopped through the pump driver circuit 320, opens the on-off valve 33, and air to be discharged in the fluid bag 21. The CPU 100 displays a measurement result of the blood pressure value on the display 50, and also records the measurement result in the memory 51. Note that the calculation of the blood pressure value is not limited to the pressurization process, and may be performed in a decompression process.

Since only the pulse wave detection unit 40E and the first contact electrode 61 are present between the external surface portion of the fluid bag 21 that constitutes the inner circumferential portion 20a of the belt portion 20 and the left wrist 90, the compression by the fluid bag 21 is not inhibited by other members, and a blood vessel can be sufficiently closed. Therefore, the blood pressure measurement by the oscillometric method can be performed with high accuracy.

The CPU 100 performs a calibration between the blood pressure value measured by the oscillometric method and the pulse transit time $\Delta t$, and thus associates the blood pressure value and the pulse transit time $\Delta t$ with each other. As a result, it is possible to estimate the blood pressure value based on the pulse transit time $\Delta t$.

In the blood pressure estimation device 1 according to the present embodiment, when the ECG pulse is detected, the second contact electrode 62 is pressed by the subject from the outer circumferential side of the belt portion 20, and thus the pulse wave detection unit 40E is configured to be pressed into close contact with the target measurement site. Detection accuracy of a pulse wave of the radial artery 91 is increased by detecting the pulse wave of the radial artery 91 in this state, and measurement accuracy of a pulse transit time (PTT) can be increased. In turn, the accuracy of the blood pressure estimation device 1 can be increased. The second contact electrode 62 is located, on the outer circumferential portion 20b of the belt portion 20 in a state of surrounding the target measurement site, on a side opposite to the display unit 10 in the circumferential direction of the belt portion 20. Thus, the pulse wave of the radial artery 91 can be effectively detected while the display unit 10 is located on the left wrist 90 of the subject on the back side of the hand.

In the blood pressure estimation device 1 according to the present embodiment, the notification unit 58 notifies a determination result of whether or not the detection accuracy of a pulse wave by the pulse wave detection unit 40E satisfies a reference value. Specifically, the CPU 100 determines whether or not a signal-noise ratio (SN ratio) of the detected pulse wave of the radial artery 91 satisfies the reference value.

When the SN ratio is less than the reference value, the CPU 100 transmits a signal to the notification unit 58, and causes LED light that is the notification unit 58 to emit red light, for example. When the SN ratio is greater than or equal to the reference value, the CPU 100 transmits a signal to the notification unit 58, and causes LED light that is the notification unit 58 to emit blue light, for example. In this way, it is possible to notify the subject whether or not the pressing of the second contact electrode 62 is sufficient.

In the blood pressure estimation device 1 according to the present embodiment, blood pressure estimation accuracy during a Valsalva load or a cold load, for example, can be highly maintained by estimating a blood pressure value with, as the pulse transit time (PTT), the time difference Δt between a peak of the ECG pulse and a peak of the pulse wave of the radial artery.

The blood pressure estimation device 1 according to the present embodiment includes the fluid bag 21, the pressure sensor 31, the oscillation circuit 310, the pump 32, the pump drive circuit 320, and the on-off valve 33 for performing a blood pressure measurement by the oscillometric method, but may not necessarily include these. When the blood pressure estimation device 1 does not include these, a blood pressure measurement by the oscillometric method is performed by another device, a calibration is performed on a blood pressure measurement value thereof and the pulse transit time Δt, and thus the blood pressure value and the pulse transit time Δt are associated with each other. In such a case, it is also possible to estimate the blood pressure value based on the pulse transit time Δt. Note that, in this case, the first contact electrode 61 and the pulse wave detection unit 40E of the pulse wave sensor are provided on the inner circumferential portion 23a of the belt body 23.

Second Embodiment

Hereinafter, a blood pressure estimation device according to a second embodiment of the present invention will be described with reference to the drawings. Note that the blood pressure estimation device according to the second embodiment of the present invention is different from the blood pressure estimation device 1 according to the first embodiment only in that the blood pressure estimation device according to the second embodiment includes a solid member disposed between a belt body and a fluid bag, and thus description of a configuration similar to that of the blood pressure estimation device 1 according to the first embodiment will not be repeated.

Figure 8:
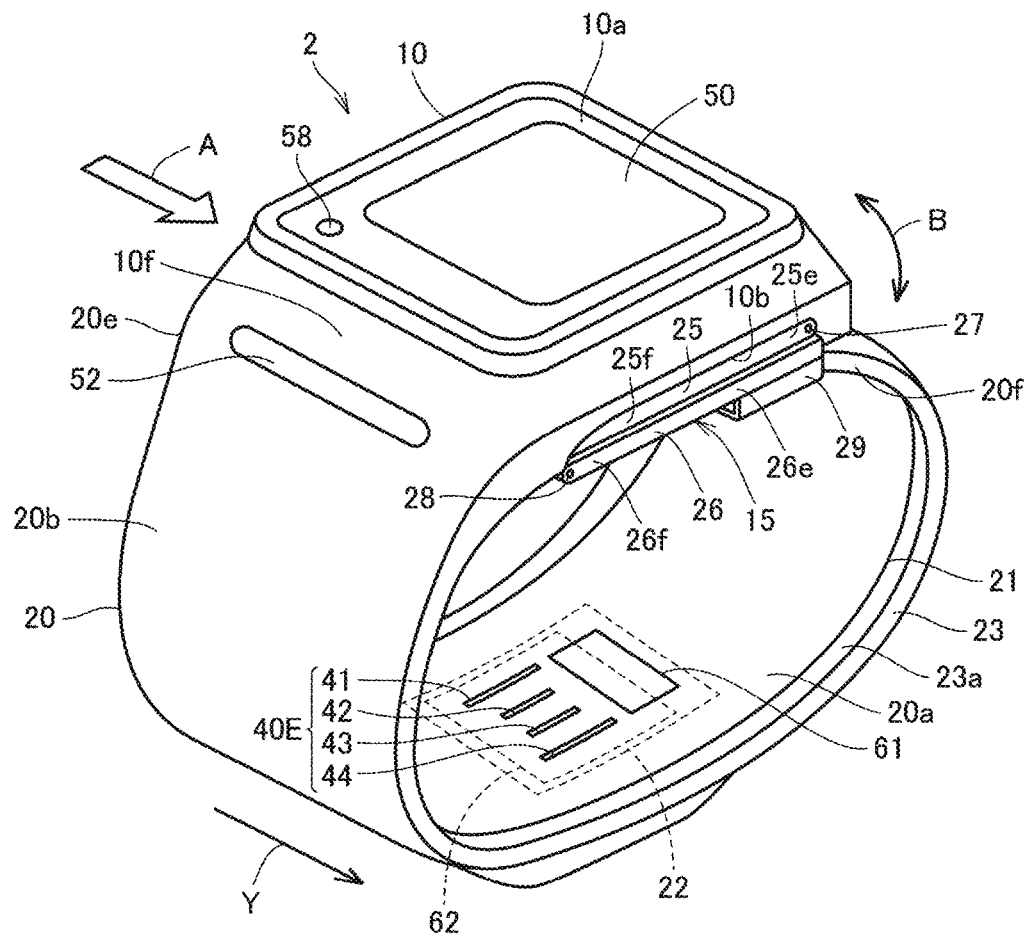
FIG. 8 is a perspective view illustrating an appearance of a blood pressure estimation device according to a second embodiment of the present invention.
Figure 9:
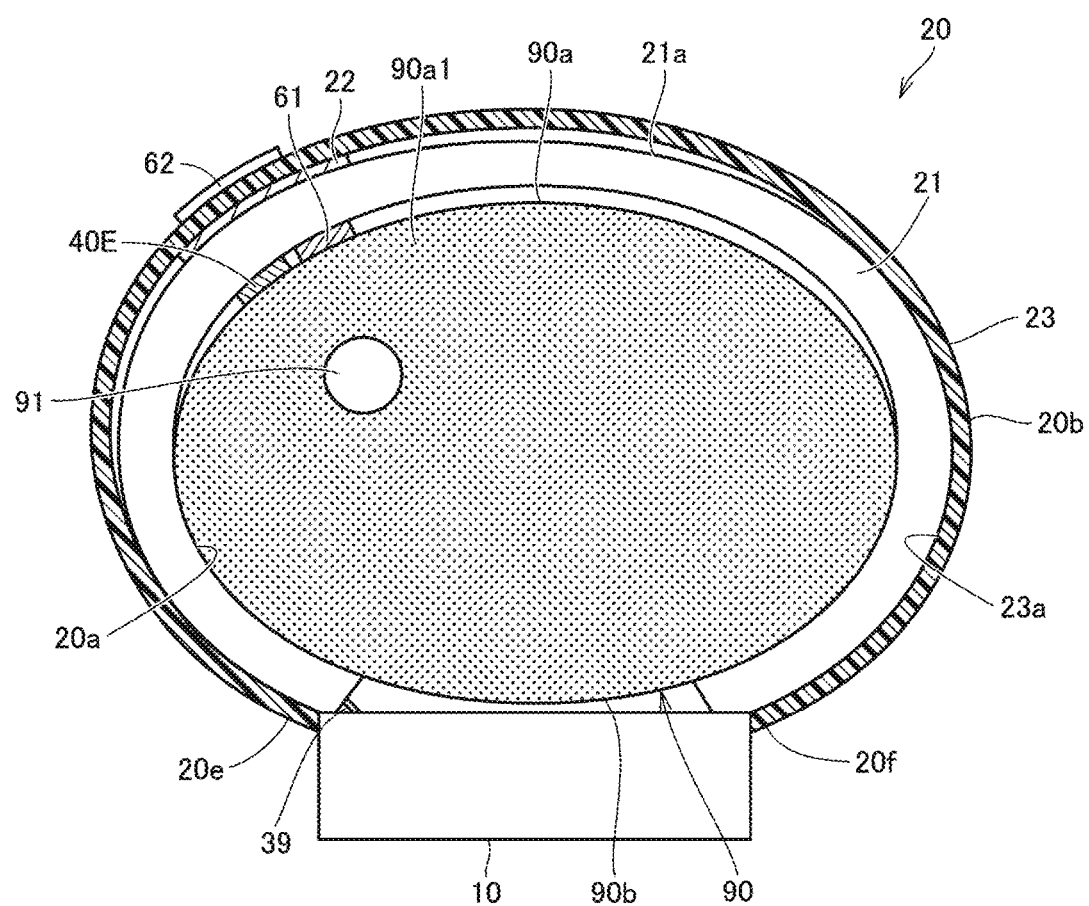
FIG. 9 is a cross-sectional view illustrating a state in which the blood pressure estimation device according to the second embodiment of the present invention is attached to a target measurement site.

FIG. 8 is a perspective view illustrating an appearance of the blood pressure estimation device according to the second embodiment of the present invention. FIG. 9 is a cross-sectional view illustrating a state in which the blood pressure estimation device according to the second embodiment of the present invention is attached to a target measurement site. In the present embodiment, the target measurement site is a left wrist. In FIG. 9, a cross section perpendicular to a longitudinal direction of the left wrist is illustrated. Note that the target measurement site may be a right wrist.

As illustrated in FIGS. 8 and 9, a blood pressure estimation device 2 according to the second embodiment of the present invention includes a display unit 10, a belt portion 20, a first contact electrode 61 and a second contact electrode 62 for detecting an electrocardiographic waveform, and a pulse wave sensor.

The belt portion 20 includes a belt body 23, and a fluid bag 21 that is provided on an inner circumferential side of the belt body 23 and is inflatable and deflatable. The belt portion 20 further includes a solid member 22 disposed between the belt body 23 and the fluid bag 21.

The solid member 22 faces at least a part of the second contact electrode 62 with the belt body 23 interposed therebetween, and faces at least a part of a pulse wave detection unit 40E with the fluid bag 21 interposed therebetween. The solid member 22 is curved so as to conform to a shape of the target measurement site.

In the present embodiment, the entirety of the pulse wave detection unit 40E faces the solid member 22 with the fluid bag 21 interposed therebetween. The entirety of the first contact electrode 61 faces the solid member 22 with the fluid bag 21 interposed therebetween. The entirety of the second contact electrode 62 faces the solid member 22 with the belt body 23 interposed therebetween.

The solid member 22 is bonded to each of an inner circumferential portion 23a of the belt body 23 and an external surface portion 21a of the fluid bag 21 that faces the inner circumferential portion 23a of the belt body 23. The solid member 22 is formed of a resin such as plate-like polypropylene having a thickness of greater than or equal to 1 mm and less than or equal to 2 mm, for example.

Figure 10:
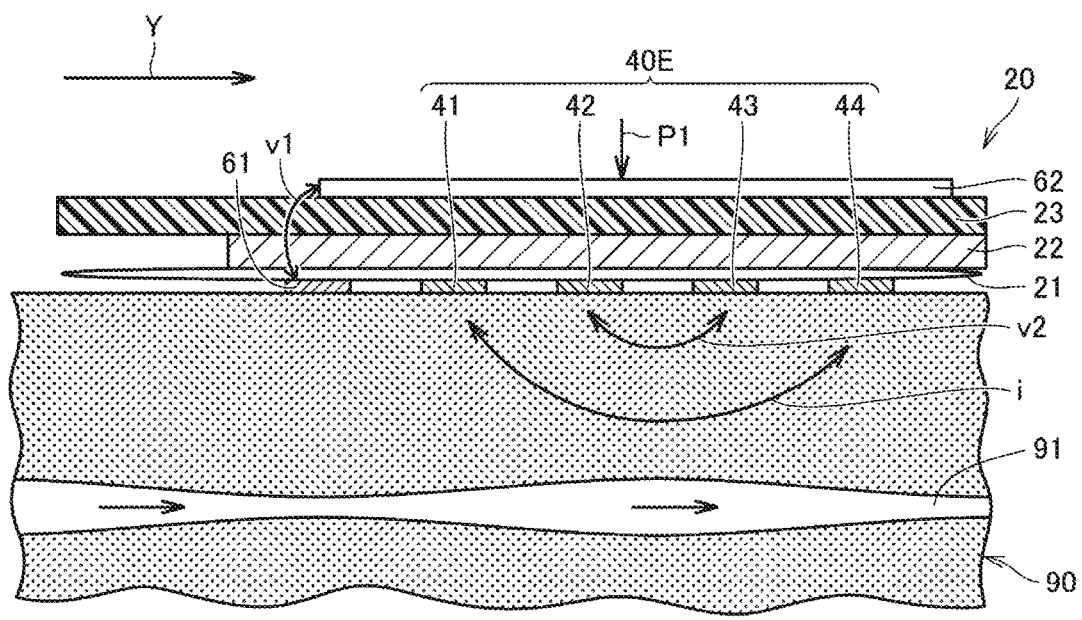
FIG. 10 is a cross-sectional view illustrating a state in which the blood pressure estimation device according to the second embodiment of the present invention is attached to the target measurement site and measures a pulse transit time.

FIG. 10 is a cross-sectional view illustrating a state in which the blood pressure estimation device according to the second embodiment of the present invention is attached to the target measurement site and measures a pulse transit time. In FIG. 10, the cross section along the longitudinal direction of the left wrist is illustrated. Note that a position of the first contact electrode 61 is changed and illustrated for convenience of description.

As illustrated in FIG. 10, when an ECG pulse and a pulse wave of a radial artery 91 are detected, a subject presses the second contact electrode 62 with a finger of a right hand. As a result, a pressing force P1 is applied to the second contact electrode 62, and the pulse wave detection unit 40E is pressed against the target measurement site via the solid member 22. By pressing the pulse wave detection unit 40E against the target measurement site via the solid member 22, each of a current electrode 41, a detection electrode 42, a detection electrode 43, and a current electrode 44 can be pressed against the target measurement site with a uniform pressing force, detection accuracy of the pulse wave of the radial artery 91 is increased, and measurement accuracy of a pulse transit time (PTT) can be increased. In turn, the accuracy of the blood pressure estimation device 2 can be increased.

Further, since the solid member 22 is curved so as to conform to the shape of the target measurement site, each of the current electrode 41, the detection electrode 42, the detection electrode 43, and the current electrode 44 can be pressed against the target measurement site with a more uniform pressing force.

Furthermore, the entirety of the first contact electrode 61 faces the solid member 22 with the fluid bag 21 interposed therebetween, and thus the entirety of the first contact electrode 61 can be brought into close contact with the target measurement site. As a result, detection accuracy of the ECG pulse is increased, and the measurement accuracy of the pulse transit time (PTT) can be increased. In this way, the accuracy of the blood pressure estimation device 2 can also be increased.

Note that the above-described embodiments disclosed herein are illustrative in all respects and are not to be construed as a basis for limiting interpretation. Therefore, the technical scope of the present invention is not to be interpreted by only the embodiments described above, and is defined based on the description of the claims. Further, the scope of the present invention includes all meaning equivalent to the scope and changes within the scope.

REFERENCE SIGNS LIST

1, 2 Blood pressure estimation device
Display unit

10a Top surface portion
10b Bottom surface
10f Side surface portion
15 Buckle
20 Belt portion
20a, 23a Inner circumferential portion
20b Outer circumferential portion
20e, 20f, 25e, 25f, 26e, 26f End portion
21 Fluid bag
21a External surface portion
22 Solid member
23 Belt body
25, 26 Plate-like member
27, 28 Connecting rod
29 Fixing portion
31 Pressure sensor
32 Pump
33 On-off valve
38, 39 Air pipe
40 Pulse wave sensor
40E Pulse wave detection unit
41, 44 Current electrode
42, 43 Detection electrode
49, 69 Voltage detection circuit
50 Display
51 Memory
52 Operating section
53 Battery
58 Notification unit
59 Communication unit
60 Measurement unit
61 First contact electrode
62 Second contact electrode
71, 72, 73 Wire
90 Left wrist
90a Palm side surface
90a1 Portion
90b Back side surface
91 Radial artery
310 Oscillation circuit
320 Pump drive circuit
900 Network

The invention claimed is:

1. A blood pressure estimation device, comprising:
a display unit configured to display a blood pressure estimation result;
a belt portion that is connected to the display unit and surrounds a target measurement site;
a first contact electrode and a second contact electrode for detecting an electrocardiographic waveform; and
a pulse wave sensor including a pulse wave detection unit configured to detect a pulse wave of an artery passing through the target measurement site, wherein
the first contact electrode and the pulse wave detection unit are provided on an inner circumferential portion of the belt portion,
the second contact electrode is provided on an outer circumferential portion of the belt portion to overlap at least one portion of the first contact electrode provided on the inner circumferential portion of the belt portion, and
the first contact electrode and the pulse wave detection unit are provided in a position where the first contact electrode and the pulse wave detection unit are to be pressed against the target measurement site when the second contact electrode is pressed from an outer circumferential side of the belt portion.

2. The blood pressure estimation device according to claim 1, wherein
at least a part of the pulse wave detection unit and at least a part of the second contact electrode face each other with the belt portion interposed therebetween.

3. The blood pressure estimation device according to claim 1, wherein
the belt portion includes a belt body and a fluid bag that is provided on an inner circumferential side of the belt body and external surface is inflatable and deflatable,
a pressure sensor configured to detect pressure in the fluid bag is provided,
the first contact electrode and the pulse wave detection unit are provided on a portion of the fluid bag that constitutes the inner circumferential portion of the belt portion, and
the second contact electrode is provided on an external surface portion of the belt body that constitutes the outer circumferential portion of the belt portion.

4. The blood pressure estimation device according to claim 3, wherein
the belt portion further includes a solid member disposed between the belt body and the fluid bag, and
the solid member faces at least a part of the second contact electrode with the belt body interposed therebetween, and faces at least a part of the pulse wave detection unit with the fluid bag interposed therebetween.

5. The blood pressure estimation device according to claim 4, wherein
the solid member is curved so as to conform to a shape of the target measurement site.

6. The blood pressure estimation device according to claim 1, wherein
the pulse wave detection unit detects a pulse wave based on a change in impedance of the artery passing through the target measurement site.

7. The blood pressure estimation device according to claim 1, further comprising
a notification unit configured to notify a determination result of whether or not detection accuracy of a pulse wave by the pulse wave detection unit satisfies a reference value.

8. The blood pressure estimation device according to claim 1, wherein
the second contact electrode is located, on the outer circumferential portion of the belt portion in a state of surrounding the target measurement site, on a side opposite to the display unit in a circumferential direction of the belt portion.

* * * * *